United States Patent [19]

Sundelin

[11] 4,421,751
[45] Dec. 20, 1983

[54] BIPYRIDINE SUBSTITUTED IMIDAZOYLIDENE, COPPER COMPLEX, AND ITS USE IN FOOD-PRODUCING ANIMALS

[75] Inventor: Kurt G. R. Sundelin, Modesto, Calif.

[73] Assignee: International Minerals & Chemical Corp., Terre Haute, Ind.

[21] Appl. No.: 364,369

[22] Filed: Apr. 1, 1982

[51] Int. Cl.³ .................. A61K 31/555; A61K 31/44; C07D 401/00; C07F 15/00
[52] U.S. Cl. .................................... 424/245; 424/263; 546/2; 546/9; 546/256
[58] Field of Search .................... 424/263, 245; 546/9, 546/256, 2

[56] References Cited

U.S. PATENT DOCUMENTS 3,252,802  5/1966  Cunningham .............................. 99/2

OTHER PUBLICATIONS

*J. Am. Chem. Soc.*, 74, 5193–5195, (1952).

*J. Org. Chem.*, 2562–2565, (1975).

*Primary Examiner*—Frederick E. Waddell
*Attorney, Agent, or Firm*—Steven R. Lammert

[57] ABSTRACT

Certain novel bipyridine substituted imidazoylidene compounds, their metal complexes (Cu, Fe and Ni) which are effective to improve feed efficiency and promote growth in food-producing animals, particularly ruminants. The compounds are described by the general formula

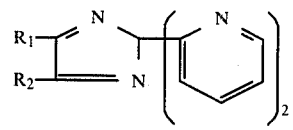

in which $R_1$ and $R_2$ are hydrogen, alkyl or phenyl, and including the cuprous, nickelous and ferrous salts thereof.

11 Claims, No Drawings

BIPYRIDINE SUBSTITUTED IMIDAZOYLIDENE, COPPER COMPLEX, AND ITS USE IN FOOD-PRODUCING ANIMALS

BACKGROUND

There is an ever-increasing need for efficiency in producing animal protein for human consumption. As world population continues to increase, available animal feed materials increase in price, and it becomes most important that maximum growth potential from available feed materials be realized.

In monogastric food-producing animals such as swine and poultry, feed additives may be employed to protect against subclinical gastrointestinal infections, and thereby enable the target animal to realize its greatest food-producing potential. When such animals receive such feed additives on a daily basis at low levels, greater control of parasitic infections, such as coccidiosis, can be realized, and more of the feed goes to growth.

In ruminant animals such as cattle, goats and sheep, significant improvements in feed efficiency and growth can be obtained by chemical modification of the metabolism of rumen microorganisms. This may be accomplished by reducing the proportion of methane formed, and increasing the proportion of propionate at the expense of methane and acetate. Methane tends to be formed during fermentation of food in the ruminant. This represents a loss in feed energy intake, because the methane gas is lost by eructation.

Propionic acid is a much more efficient precursor of glucose, from which the animal derives its energy and growth, than acetic acid. It is, therefore, most desirable to shift the balance of rumen metabolism toward propionate production to obtain more efficient feed utilization and to promote growth in ruminants.

SUMMARY

The subject invention is directed to certain novel bipyridine substituted imidazoylidene compounds, their copper complexes, and their use to improve feed efficiency and promote growth in food-producing animals, particularly in ruminants. These imidazoylidene compounds are described by the general formula:

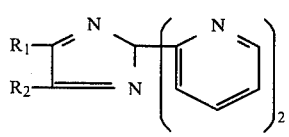

wherein $R_1$ and $R_2$ are hydrogen, alkyl, or phenyl. Also included in the useful compounds are the cuprous, ferrous and nickelous salts of the compounds of Formula I. The pyridine groups are both connected to the imidazoylidene ring at the number two carbon thereof. A particularly preferred compound of the above general formula is:

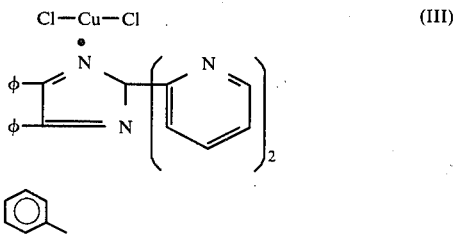

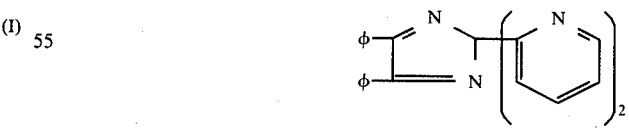

which may be described as 2,2'-(4,5-diphenyl-2H-imidazol-2-ylidene)bispyridine with $CuCl_2$ (1/1). The above compound is a light green solid, and has a melting point of 299°–300° C. The calculated analysis is: C-59%; H-3.6%; N-11%; Cl-13.9%; Cu-(Balance). The above composition is particularly useful for growth promotion in ruminants. The compound may be administered orally in the form of physiologically acceptable salt, the above copper chloride salt being preferred. The compound is preferably administered as a feed additive, but it may take the form of a bolus which is capable of controlled release in the rumen over a predetermined period of time. Other oral administration methods include, e.g. as a drench, intubation, as a liquid supplement in solutions, suspensions, dispersions or emulsions. It is possible also to administer the composition parenterally as by injection, or by subcutaneous implant combined in implant pellet form with a suitable excipient, such as lactose, polylactides, collagen, starch, magnesium stearate, vegetable gum, cellulose acetate, dimethylpolysiloxane, ethylene vinyl acetate, or other inert, biocompatible material.

DESCRIPTION OF PREFERRED EMBODIMENTS

EXAMPLE 1

The base composition was made as set forth below:

Benzil

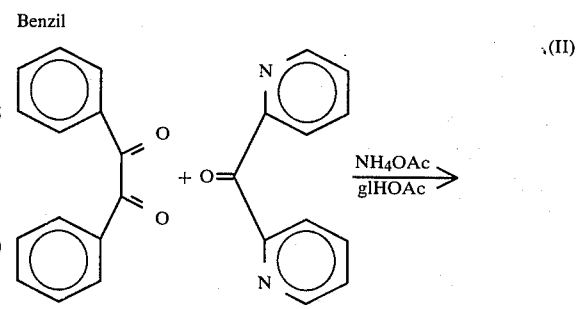

Benzil is reacted with di-2-pyridyl ketone in the presence of ammonium acetate and glacial acetic acid to produce 2,2'-(4,5-diphenyl-2H-imidazol-2-ylidene)bispyridine, a tan solid having a melting point of 214°–216° C. and a molecular weight of 374.4. The above benzil and di-2-pyridyl ketone compounds were obtained from Aldrich Chemicals, Inc., Milwaukee, Wis. The ammonium acetate and glacial acetic acid were obtained from Mallinkrodt Chemicals, Inc., St. Louis, Mo.

The above compound was then reacted with anhydrous cuprous chloride (CuCl₂) dissolved in hot, absolute alcohol as follows:

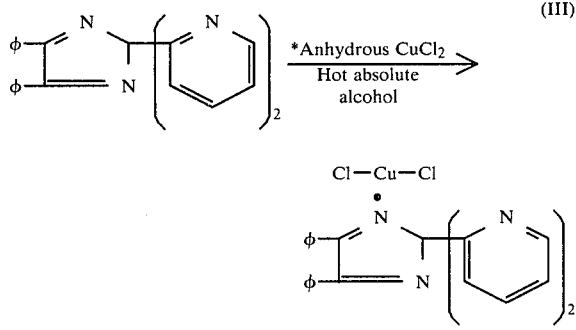

*CuCl₂ hydrate was dried at 100° C. in vacuo.

The above reaction formed an immediate emerald green precipitate, but the mixture was allowed to stir for three days, after which the resulting solid was removed by filtration and washed with alcohol to yield: 2,2'-(4,5-diphenyl-2H-imidazol-2-ylidene)bispyridine complexed with $CuCl_2$ (1/1). This latter composition had a melting point of 299°–300° C. Molecular weight was about 508.8.

EXAMPLE 2

The above Formula III composition was tested to determine its effectiveness as a feed additive for ruminants. The initial tests were in rumen fluid batch culture systems to determine the effect of the compound on volatile fatty acid/methane ratios (VFA/CH₄). The subject compound was used at concentrations of 8.33, 25 and 75 ppm, and the effects compared to a positive control, monensin, at 12.5 ppm. A summary of the VFA, gas (CH₄+H₂) production, and protein and amino acid accumulation are presented in Table 1. Test Procedure: A 50/50 mixture of ground corn and ground alfalfa was used as the substrate for the subject rumen fluid batch culture test. The compound (Formula III) was present in the rumen fluid in three separate test samples at 8.33, 25 and 75 ppm, respectively.

On day 1, rumen fluid was obtained from mature fistulated steers on 50/50 concentrate/roughage diets. The rumen fluid (RF) was strained through three layers of gauze cloth and equilibrated with CO₂ gas. Wheaton serum vials (125 ml) were prepared ahead with 20 ml continuous batch buffer and 100 mg 50/50 ground corn/ground alfalfa. Controls and compounds (dissolved in acetone) were set up according to desired levels. The vials were kept under CO₂ gas until 20 ml of the strained RF was added. The vials were sealed and incubated at 39° C. for 24 hours in a hot water bath. On successive days, gas samples (0.1 ml) were drawn for gas chromatography analysis before transferring 20 ml of the batch culture to another vial containing 20 ml of buffer, 100 mg substrate, and the corresponding compound. The remaining 20 ml was inoculated with 2 ml 6 N HCl and centrifuged at 15,000 rpm for 15 minutes. Ether extracts were prepared for volatile fatty acid (VFA) analysis. Some minor adjustments were made in the temperatures on the Hewlett-Packard 5750 Gas-Liquid Chromatograph used for VFA analysis when the glass column used as changed from ¼ inch diameter to ⅛ inch diameter.

Injection Port = 220° C.
Column Oven = 170° C.
Flame Detector = 250° C. Only 4 minutes was needed to record the sample instead of the previous 7 minutes.

Results: Table 1 lists a summary of the VFA and gas data which is given in percent change from the controls.

The Formula III compound increased propionate and decreased acetate at all levels tested, and this effect appeared to be dose related. At 8.33 μg/ml, methane was decreased slightly. At 25 and 75 μg/ml, there were slight decreases in methane during the first 6 days with no hydrogen production. On the seventh day, methane dropped drastically at these two levels, and there was some hydrogen produced. At 25 μg/ml, methane production seemed to be recovering by day 10, but at 75 μg/ml, methane was inhibited completely. Amino acid accumulation at 75 μg/ml was similar to that observed with monensin. Table 2 shows the total volatile fatty acids (VFA), methane and hydrogen produced at day 10, and Table 3 shows the caloric values of these various products.

The Formula III compound caused increased proprionate and decreased acetate production, which resulted in more of the energy appearing in propionate. Except for the 25 μg/ml concentration, more butyrate was produced in the presence of the Formula III compound than was produced by the control. Total energy in the end products appeared to be less than the control at 8.33 and 25 μg/ml.

TABLE 1

Summary of the Volatile Fatty Acid and Gas Production and Protein and Amino Acid Accumulation[a]

| Treatment | Day | HFo[b] | HAc | HPr | HiBu | HBu | HiVal | Total | μMoles CH₄ | H₂ | mg/ml Protein | μMoles/ml AA |
|---|---|---|---|---|---|---|---|---|---|---|---|---|
| Control | 2 | 1.35 | 42.26 | 10.82 | 1.43 | 10.62 | 0.81 | 67.28 | 220 | 0 | 0 | 0.26 |
|  | 3 | 0.97 | 38.28 | 11.69 | 1.00 | 10.02 | 2.59 | 64.53 | 184 | 0 | 0 | 0.17 |
|  | 4 | 1.26 | 36.04 | 12.17 | 1.16 | 9.10 | 2.91 | 62.62 | 184 | 0 | —[c] | — |
|  | 5 | 0.96 | 30.16 | 10.06 | 0.76 | 6.68 | 0.77 | 49.37 | 201 | 0 | — | — |
|  | 6 | 0.78 | 29.48 | 9.45 | 0.74 | 4.21 | 0.17 | 44.82 | 193 | 0 | 0 | 0.15 |
|  | 7 | 0.84 | 31.35 | 10.92 | 0.49 | 4.22 | 0 | 47.81 | 176 | 0 | 0 | 0.14 |
|  | 8 | 0.56 | 30.16 | 11.07 | 0.75 | 5.42 | 0 | 47.94 | 195 | 0 | 0 | 0.12 |
|  | 9 | 0.63 | 29.33 | 10.86 | 0.50 | 4.68 | 0.69 | 46.63 | 186 | 0 | 0 | 0.18 |
|  | 10 | 0.14 | 28.55 | 9.40 | 0.04 | 3.01 | 0.99 | 42.11 | 187 | 0 | 0 | 0.25 |
| Monensin 12.5 μg/ml | 2 | 1.07 | 26.75 | 15.68 | 2.26 | 14.56 | 0.60 | 60.90 | 68 | 0 | 0.05 | 0.51 |
|  | 3 | 0.92 | 24.86 | 16.63 | 1.26 | 9.75 | 1.91 | 55.32 | 39 | 0 | 0.07 | 0.28 |
|  | 4 | 1.04 | 24.82 | 20.16 | 1.41 | 7.58 | 1.98 | 56.98 | 32 | 0 | — | — |
|  | 5 | 1.00 | 17.11 | 14.20 | 0.51 | 2.50 | 0.08 | 35.39 | 23 | 0 | — | — |
|  | 6 | 1.32 | 20.01 | 16.87 | 0.50 | 2.48 | 0 | 41.18 | 25 | 0 | 0.05 | 0.29 |
|  | 7 | 1.53 | 20.02 | 19.11 | 1.34 | 5.52 | 1.16 | 48.68 | 32 | 0 | 0.05 | 0.34 |
|  | 8 | 0.90 | 21.24 | 18.34 | 0.53 | 2.58 | 0.33 | 43.90 | 41 | 0 | 0.03 | 0.30 |
|  | 9 | 0.72 | 18.75 | 16.30 | 0.48 | 2.15 | 0 | 38.49 | 51 | 0 | 0.04 | 0.30 |

TABLE 1-continued
Summary of the Volatile Fatty Acid and Gas Production and Protein and Amino Acid Accumulation[a]

| Treatment | Day | HFo[b] | HAc | HPr | HiBu | HBu | HiVal | Total | μMoles CH$_4$ | H$_2$ | mg/ml Protein | μMoles/ml AA |
|---|---|---|---|---|---|---|---|---|---|---|---|---|
| | 10 | 0.75 | 21.91 | 20.51 | 0.59 | 3.47 | 0.08 | 47.28 | 49 | 0 | 0 | 0.44 |
| Formula III | 2 | 1.48 | 43.83 | 11.81 | 1.27 | 12.33 | 0 | 70.71 | 204 | 0 | 0 | 0.16 |
| Compound | 3 | 0.92 | 33.35 | 12.17 | 1.14 | 9.87 | 1.14 | 58.58 | 157 | 0 | 0 | 0.13 |
| 8.33 μg/ml | 4 | 0.40 | 34.54 | 13.16 | 0.68 | 7.77 | 2.01 | 58.54 | 164 | 0 | — | — |
| | 5 | 0.30 | 33.15 | 12.66 | 0.35 | 7.14 | 1.17 | 54.76 | 181 | 0 | — | — |
| | 6 | 1.02 | 29.32 | 11.08 | 0.46 | 5.69 | 0 | 47.57 | 176 | 0 | 0 | 0.11 |
| | 7 | 0.73 | 29.53 | 13.12 | 0.76 | 4.39 | 0.77 | 49.29 | 139 | 0 | 0 | 0.11 |
| | 8 | 0.55 | 26.19 | 13.48 | 0.65 | 5.49 | 2.20 | 48.55 | 158 | 0 | 0 | 0.09 |
| | 9 | 0.50 | 27.31 | 13.73 | 0.58 | 3.06 | 0.55 | 45.71 | 157 | 0 | 0 | 0.10 |
| | 10 | 0.23 | 24.52 | 12.89 | 0.21 | 2.56 | 0.05 | 40.45 | 159 | 0 | 0 | 0.24 |
| Formula III | 2 | 1.24 | 46.39 | 12.69 | 1.66 | 10.94 | 2.55 | 75.45 | 197 | 0 | 0 | 0.16 |
| Compound | 3 | 1.05 | 35.36 | 12.93 | 1.21 | 7.27 | 0.59 | 58.40 | 166 | 0 | 0 | 0.17 |
| 25 μg/ml | 4 | 0.71 | 36.52 | 14.32 | 0.86 | 6.38 | 1.33 | 60.11 | 164 | 0 | — | — |
| | 5 | 0.44 | 34.06 | 14.87 | 0.56 | 6.63 | 0.78 | 57.33 | 170 | 0 | — | — |
| | 6 | 0.68 | 28.98 | 13.87 | 0.53 | 4.26 | 0.20 | 48.49 | 143 | 0 | 0.01 | 0.11 |
| | 7 | 0.61 | 22.54 | 13.54 | 0.75 | 5.02 | 0.51 | 42.95 | 58 | 8 | 0 | 0.24 |
| | 8 | 2.20 | 20.38 | 14.71 | 2.73 | 8.39 | 0 | 48.40 | 6 | 17 | 0 | 0.22 |
| | 9 | 1.78 | 20.91 | 14.96 | 1.21 | 5.82 | 0 | 44.66 | 28 | 22 | 0.03 | 0.20 |
| | 10 | 1.00 | 21.76 | 13.79 | 0.01 | 2.06 | 0 | 38.62 | 55 | 8 | 0 | 0.30 |
| Formula III | 2 | 0.95 | 33.48 | 11.10 | 0.95 | 8.18 | 0.69 | 55.34 | 155 | 0 | 0 | 0.18 |
| Compound | 3 | 0.80 | 28.66 | 14.81 | 3.81 | 15.10 | 0.44 | 63.61 | 71 | 0 | 0.04 | 0.27 |
| 75 μg/ml | 4 | 1.29 | 27.47 | 18.71 | 0.95 | 5.26 | 0.25 | 53.92 | 74 | 0 | — | — |
| | 5 | 0.61 | 23.84 | 17.24 | 0.51 | 4.59 | 0.26 | 47.03 | 74 | 0 | — | — |
| | 6 | 0.51 | 25.01 | 16.43 | 0.39 | 1.78 | 0.58 | 44.68 | 67 | 0 | 0.02 | 0.20 |
| | 7 | 3.17 | 19.59 | 14.41 | 0.83 | 9.9 | 0.10 | 48.01 | 3 | 2 | 0.01 | 0.26 |
| | 8 | 3.52 | 17.86 | 14.08 | 2.61 | 11.25 | 0 | 49.31 | 3 | 7 | 0 | 0.31 |
| | 9 | 2.61 | 18.93 | 13.41 | 3.16 | 9.21 | 0.26 | 50.56 | 0 | 11 | 0 | 0.34 |
| | 10 | 2.52 | 18.71 | 14.57 | 3.74 | 8.16 | 0.27 | 47.97 | 0 | 14 | 0 | 0.47 |

[a]Each value is the mean of duplicate serum vials.
[b]HFo = formate, HAc = acetate, HPr = propionate, HiBu = isobutyrate, HBu = butyrate, HiVal = isovalerate.
[c]Not determined.

TABLE 2
Total VFA's and Gas Produced on Day 10

| Treatment | Conc (μg/ml) | HFo[a] | HAc | HPr | HiBu | HBu | HiVal | Total | CH$_4$ | H$_2$ |
|---|---|---|---|---|---|---|---|---|---|---|
| Control | — | 0 | 555.2 | 158.8 | 0 | 26.8 | 25.6 | 766.4 | 187 | 0 |
| Monensin | 12.5 | 15.60 | 501.6 | 494.4 | 14.0 | 96.8 | 3.2 | 1,125.6 | 49 | 0 |
| Formula III Compound | 8.33 | 0 | 434.4 | 240.8 | 0 | 41.2 | 0 | 716.4 | 159 | 0 |
| Formula III Compound | 25 | 4.40 | 452.4 | 252.4 | 0 | 0 | 0 | 709.2 | 55 | 8 |
| Formula III Compound | 75 | 48.8 | 369.6 | 314.4 | 86.4 | 142.4 | 5.6 | 994.2 | 0 | 14 |

[a]HFo = formate, HAc = acetate, HPr = propionate, HiBu = isobutyrate, HBu = butyrate, HiVal = isovalerate.

It can be seen from the above Table that the Formula III compound, at all dosage levels provided the desired shift in volatile fatty acids produced away from acetate towards propionate. At the 75 ppm dosage level, the shift away from acetate production, and the increase in propionate production was most evident.

Table 3 below further confirms that the Formula III compound is effective to shift the volatile fatty acid production from acetate to propionate. The 75 ppm dosage level of the Formula III compound was the most effective amount for increasing the number of calories available from the animals' feed.

TABLE 3
Caloric Value[a] of VFA's, CH$_4$ and H$_2$ Produced on Day 10

| Treatment | Conc (μg/ml) | HFo | HAc | HPr | HiBu | HBu | HiVal | Total | CH$_3$ | H$_2$ | Total Cal in VFA and Gas | Gross Calories Remaining in Feed[b] |
|---|---|---|---|---|---|---|---|---|---|---|---|---|
| Control | — | 0 | 116.26 | 57.96 | 0 | 13.94 | 17.38 | 205.54 | 39.42 | 0 | 244.96 | 208.21 |
| Monensin | 12.4 | 0.98 | 105.04 | 180.46 | 5.11 | 50.34 | 2.17 | 344.10 | 10.33 | 0 | 354.43 | 364.76 |
| Formula III Compound | 8.33 | 0 | 90.96 | 87.89 | 0 | 21.42 | 0 | 200.27 | 33.52 | 0 | 233.79 | 263.51 |
| Formula III Compound | 25 | 0.28 | 94.73 | 92.13 | 0 | 0 | 0 | 187.14 | 11.59 | 0.55 | 199.28 | 297.38 |
| Formula III Compound | 75 | 3.06 | 77.39 | 114.76 | 31.54 | 74.05 | 3.80 | 304.60 | 0 | 0.96 | 305.56 | 350.70 |

[a]1 mole HFo = 62.8 kcal, 1 mole HAc = 209.4 kcal, 1 mole HPr = 365 kcal, 1 mole, 1 mole HiBu = 517.4 kcal, 1 mole HBu = 520 kcal, 1 mole HiVal = 679 kcal, 1 mole CH$_4$ = 210.8 kcal, 1 mole H$_2$ = 68.3 kcal.
[b]Initial feed gross energy was 800 kcal.

EXAMPLE 3

The subject Formula III compound was also compared to monensin in another rumen fluid batch culture test as set forth below. The test was designed to screen compounds for inhibition of starch breakdown by the rumen microflora. In this test, the rumen fluid batch culture containing 50 ppm of the Formula III compound degraded only 28.7% starch relative to an unincubated control rumen fluid batch culture which did not contain the Formula III compound. It is considered more desirable to avoid degradation of starch in the rumen so that it is passed on into the abomasum where it can be digested more efficiently. When the concentration of the Formula III compound was increased to 75 ppm, the percent starch degraded dropped to 13.9% relative to the unincubated control without the Formula III compound. Test Procedure: Animals—Mature fistulated steers were maintained on concentrate, roughage, or concentrate/roughage (50/50) rations. Animals were fed twice daily at 8:00 A.M. and 4:00 P.M.

Rumen Fluid Sampling and Preparation for Batch Culture Assays—Approximately two liters of rumen fluid were collected from fistulated animals with the use of a hand pump. The rumen fluid, collected in a stoppered flask, was then immediately taken to the laboratory for processing. Samples were taken at 8:00 A.M. just prior to the first feeding or at 1:00 P.M. (ca. 4-5 hours after the first feeding). Rumen fluid was strained through six layers of cotton gauze cloth into a flask that was flushed with $CO_2$ gas. The filtrate was centrifuged for 5 minutes at 100 rpm in a Sorvall centrifuge to remove large particulate material. The supernatant was again passed through six layers of gauze into a flask under $CO_2$ gas and stoppered.

Batch Culture Assay for the Degradation of Starch—Twenty-five ml of rumen fluid prepared as above was added to serum vials (Wheaton Glass, 100 ml capacity) containing 0.25-1.00% final concentration starch as an energy substrate in 25 ml batch culture assay buffer. The serum vials were sealed under $CO_2$ gas phase, and incubations were carried out for 20-24 hours at 39° C. on a New Brunswick rotary shaker (250 rpm). Each experimental vial was done in triplicate. The corn starch used in degradation experiments was previously washed with distilled water several times, filtered through an 8 micron (47 mm) Millipore filter, and dried at 90° C. for 24 hours.

At intervals of 0 and 24 hours, the entire contents in vials were centrifuged at 250 rpm for 5 minutes. The supernatants were carefully removed with a pipet and the remaining "starch pellets" resuspended in water and passed through borosilicate glass microfiber prefilters (Millipore AP 20-047-00). Filters were dried in an oven for 24 hours at 90° C., cooled and then weighed. The amount of starch remaining after 24 hours' incubation was compared with the amount present at 0 hours and the percent of substrate degraded calculated. Results: The rates of starch degradation observed in this study with rumen fluid were similar to those reported by Poe et al (J. Animal Science 32:740-743, 1971).

Monensin and lasalocid were also compared to Formula III in this test procedure. At 25 ppm concentration, neither monensin or lasalocid had any effect on starch fermentation in the subject rumen fluid batch culture test of this Example 3 following the procedure outlined above.

EXAMPLE 4

Animal Test: The object of this test is to determine the effect of the test compound on methane production in growing animals (ruminants). A decrease in methane production is an indication of increased utilization of the animals' feed supply, and possibly an indication of the effectiveness of the compound as a growth promoter.

Test Procedure: The test animals are housed in special respiration calorimetry facilities during the tests so that all metabolic gases can be collected and measured.

Twelve wether lambs, weighing between 20 and 25 kg, were selected from a group of lambs purchased from the California Livestock Marketing Association. The animals were processed according to standard procedures after arrival, and they were ear tagged for identification purposes and weighed prior to being moved to the respiration calorimetry facility.

Experimental Design—The animals were fed 500 grams of a 30% concentrate diet (Table 4) twice daily.

TABLE 4

| Composition of 30% Concentrate Diet | |
|---|---|
| Alfalfa | 70% |
| Corn | 20% |
| Oats | 8.5% |
| Molasses | 1% |
| Trace Mineral Salt | 0.5% |

Vitamin A and D supplement (660 IU Vitamin A/kg and 330 IU Vitamin D/kg)

The Formula III compound was tested in three animals at a level of 75 ppm. The test period was one week. During the first 2 days of the week, animals received untreated feed. Treated feed was fed the next 3 days, and then untreated feed was fed for 2 days. Methane production was monitored during this time. Twelve animals were used, and six animals were placed in the respiration chambers at one time. The other six animals were held in metabolism cages, and fed control ration.

Drug and Diet—The Formula III compound was fed at 75 ppm in the treated diet. Amichloral was used as a positive control, and was fed to all lambs.

Feed was mixed as required. All formulations were analyzed at the end of the trial to determine compound stability.

Animal Management—Lambs were placed in metabolism cages and respiration chambers (six in each) for approximately 2 weeks before the start of the trial. Animals were switched after 1 week so that all animals have a chance to get used to being in the chambers. During this time, the animals were fed the diet to be used throughout the trial. Animals were fed twice daily at 8:00 A.M. and 4:00 P.M. and received 500 grams of feed at each feeding.

Sample Collection and Analysis—Since only the gas data on the methane was of interest, urine and feces were collected daily and discarded. Gas samples from each chamber were taken on the third day of treatment. These samples were analyzed by gas chromatography to get a qualitative measure of hydrogen production. The Formula III compound showed a significant decrease in methane production compared to the negative control when tested in growing lambs according to the above test procedure (Example 4). The Formula III compound may therefore be considered useful as a feed additive for animals, particularly ruminants, to promote growth and enhance feed efficiency.

EXAMPLE 5

The Formula II compound can be complexed with other related metal salts, in addition to copper. These metal salts of Formula II (which include salts of iron and nickel) are then evaluated in the rumen fluid batch culture tests set forth in Examples 2 and 3, and the results compared to those obtained with the copper complex (Formula III). The Formula III copper complex is preferred, and test results show that it has activity comparable to monensin.

EXAMPLE 6

The Formula II compound can be tested in a chick rye diet test system. When compared to the results obtained with a positive control, the Formula II compound shows promising activity. Useful antibiotics for the positive control comparison are penicillin or bacitracin.

I claim:

1. A compound of the formula

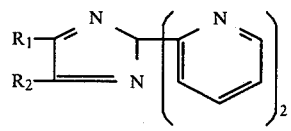

wherein $R_1$ and $R_2$ are hydrogen, alkyl or phenyl, and including the cuprous, ferrous and nickelous salts thereof.

2. A compound of the formula

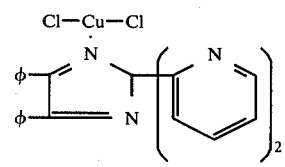

in which $\phi$ = phenyl.

3. A compound of the formula

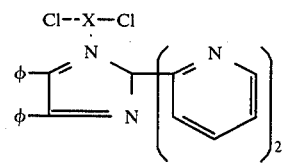

in which $X = Cu++$, $Fe++$, $Ni++$ and $\phi$ = phenyl.

4. A compound of the formula

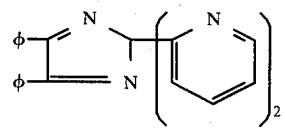

in which $\phi$ = phenyl.

5. A growth promoting animal feed additive comprising a compound of claim 1, claim 2, claim 3 or claim 4 in an amount effective to promote animal growth.

6. A growth promoting agent for animals comprising the compound of claim 2 in an amount effective to promote animal growth.

7. The method of promoting growth and enhancing feed efficiency in animals comprising administering to said animals the compound of claim 2 in an amount effective to promote growth.

8. The method of claim 7, in which the animals are ruminants.

9. The method of claim 7, in which the compound is supplied to said ruminants as an oral feed additive in an amount sufficient to obtain a growth response.

10. The method of claim 9, in which the compound is supplied to said ruminants in an amount sufficient to maintain about 75 ppm of said compound in the rumen fluid contents during the growth period of said ruminant.

11. The method of claim 7, in which the animals are poultry.

* * * * *